US00PP12588P2

(12) United States Plant Patent
Guillen

(10) Patent No.: US PP12,588 P2
(45) Date of Patent: *Apr. 30, 2002

(54) TRAILING INTERSPECIFIC IMPATIENS PLANT NAMED 'BALFAFUSIA'

(75) Inventor: Mario Guillen, Cartago (CR)

(73) Assignee: Ball Horticultural Company, West Chicago, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/473,008

(22) Filed: Dec. 28, 1999

(51) Int. Cl.[7] ..... A01H 5/00
(52) U.S. Cl. ..... Plt./317
(58) Field of Search ..... Plt./317, 318

(56) References Cited

U.S. PATENT DOCUMENTS

| | | | |
|---|---|---|---|
| PP4,720 | P | 5/1981 | Ryan |
| PP5,134 | P | 11/1983 | Mikkelsen |
| PP5,598 | P | 12/1985 | Hope |
| PP5,698 | P | 3/1986 | Hope |
| PP5,921 | P | 3/1987 | Hope |
| PP6,729 | P | 4/1989 | Kientzler |
| PP6,732 | P | 4/1989 | Kientzler |
| PP7,098 | P | 1/1990 | Drewlow |
| PP10,495 | P | 7/1998 | Danziger |
| PP10,858 | P | 4/1999 | Kientzler |

OTHER PUBLICATIONS

Stephens, L.C., Hereditas, 251–255 (1998).
Arisumi, T., *J. Amer. Soc. Hort. Sci.*, 112(6):1026–1031 (1987).
Arisumi, *The Journal of Heredity*, 64:77–79 (1973).
Arisumi, T., *J. Amer. Soc. Hort. Sci.*, 105(5):629–631 (1980).
Arisumi, T., *J. Amer. Soc. Hort. Sci.*, 110(2):273–276 (1985).
"Chapter 2—History of Commercialization" from *New Guinea Impatiens, A Ball Guide*, edited by W. Banner and M. Klopmeyer, Ball Publishing (1995).
"Chapter 20—Genetics" from *New Guinea Impatiens, A Ball Guide*, edited by W. Banner and M. Klopmeyer, Ball Publishing (1995).
"Chapter 21—Breeding for the Future"from *New Guinea Impatiens, A Ball Guide*, edited by W. Banner and M. Klopmeyer, Ball Publishing (1995).
Hortus Third A Concise Dictionary of Plants Cultivated in the United States and Canada, MacMillan Publishing Company (1976).
F1 Hybrid New Guinea Impatiens, *Ball Seed & Plant Catalog* 1999–2000, Ball Horticultural Company (1999), pp. 54–55.
Copy of U.S. application No. 09/473,386 filed on Dec. 28, 1999—"Trailing Interspecific Impatiens"—Inventor—Mario Guillen.

*Primary Examiner*—Bruce R. Campell
*Assistant Examiner*—June Hwu
(74) *Attorney, Agent, or Firm*—Gardner, Carton & Douglas

(57) ABSTRACT

A new and distinct impatiens plant named 'Balfafusia' is provided. This new cultivar was the result of a unique interspecific cross between *Impatiens flaccida* and *Impatiens Hawkeri*. More specifically, the female or seed parent of 'Balfafusia' was a proprietary *Impatiens flaccida* breeding selection and the male or pollen parent was a bulk of *Impatiens Hawkeri* pollen collected from the Java Series $F_1$ hybrid New Guinea impatiens.

1 Drawing Sheet

BACKGROUND OF THE INVENTION

The present invention comprises a new and distinctive impatiens plant, hereinafter referred to by the cultivar name 'Balfafusia'. This new cultivar was the result of a unique interspecific cross between *Impatiens flaccida* and *Impatiens Hawkeri*. More specifically, the breeding program which resulted in the production of the new cultivar was carried out at Costa Rica. The female or seed parent of 'Balfafusia' was a proprietary unnamed *Impatiens flaccida* breeding selection (non-patented) which exhibits very vigorous growth, small lavender flowers and a loose, spreading habit. The male or pollen parent of 'Balfafusia' was a bulk of *Impatiens Hawkeri* pollen collected from the Java Series $F_1$ hybrid New Guinea impatiens which exhibits medium vigor and a bushy well branched habit. The pollen was collected from several plants having a variety of flower colors and may have included orange, red, salmon, red/salmon bicolor, rose/lilac bicolor, lavender, cherry red and white. The resulting seed was collected and germinated. From the flowering progeny, a plant was selected and initally designated '2245B'. The parentage of the new cultivar can be summarized as follows:

*Impatiens flaccida*×*Impatiens Hawkeri*

Asexual reproducion of the new cultivar by terminal or stem cuttings taken during 1998 and 1999 at Arroyo Grande, Calif., U.S.A. has demonstrated that the characteristics of the new cultivar as herein described are firmly fixed and are retained through successive generations of such asexual propagation.

SUMMARY OF INVENTION

It was found that the cultivar of the present invention:

(a) exhibits a unique trailing growth habit, (b) forms medium green foliage, (c) exhibits a good basal branching character.

The Balfafusia cultivar has not been observed under all possible environmental conditions to date. Accordingly, it is possible that the phenotype may vary somewhat with variations in the environment, such as temperature, light intensity, and day length.

As shown below in Table 1, when the new cultivar of the present invention is compared to 'Grape Crush' (disclosed in U.S. Plant Pat. No. 10,107) and 'Lavender Glow' (disclosed in U.S. Plant Pat. No. 11,652), it is found to exhibit a more trailing growth habit, smaller leaves, shorter petioles and smaller flowers.

TABLE 1

| CHARACTERISTIC | 'BALFAFUSIA' | 'LAVENDER GLOW' | 'GRAPE CRUSH' |
|---|---|---|---|
| Branch length | 19.3 cm | 13 cm | |
| Branch diameter | 8 mm | 9 mm | 8 mm |
| Internode length | 4.5 cm | 4 cm | 2.6 cm |
| Leaf length | 6.3 cm | 9 cm | 0.5 cm |
| Leaf width | 2.4 cm | 3.4 cm | 3.5 cm |
| Petiole length | 11 mm | 15 mm | 20 mm |
| Flower size | 4.6 cm | 7 cm | 5.7 cm |
| Spur length | 5.5 cm | 5.3 cm | 5.5 cm |
| Spur color | 58A | 60B | 60A |
| Pollen color | 13D | 11C | 11B |

BRIEF DESCRIPTION OF THE PHOTOGRAPH

The accompanying photographs show as nearly true as it is reasonably possible to make the same in color illustrations of this type, typical flower and foliage characteristics of the new cultivar. The plants were grown in a 25 cm hanging basket with 3 plants per pot in a greenhouse at West Chicago, Ill., USA.

DETAILED BOTANICAL DESCRIPTION

The chart used in the identification of colors described herein in the R.H.S. Colour Chart of The Royal Horticultural Society, London, England. The color values were determined on Oct. 8, 1999 in West Chicago, Ill. The readings were taken between 1:00 and 1:45 p.m. under approximately 2500 footcandles of light. The plants were produced from cuttings taken from stock plants and were grown under greenhouse conditions comparable to those used in commercial practice while utilizing a soilless growth medium and maintaining temperatures of approximately 72° F. during the day and approximately 65° F. during the night. Plants used for the following descriptions and measurements were grown for 20 weeks after the planting of rooted cuttings.

Propagation:

*Type cutting.*—Terminal tip.

*Time to initate roots.*—Approximately 14–21 days with the shorter times generally being experienced in the summer and the longer times in the winter.

*Rooting habit.*—Fibrous, branching.

Botanical classification: *Impatiens flaccida*×*Impatiens Hawkeri.*

Commercial classification: Trailing Interspecific impatiens hybrid.

Plant description:

*General appearance and form.*—Trailing.

*Crop time.*—A finished flowering plant is produced 8–10 weeks after planting rooted cuttings.

*Branching habit.*—Freely basal branching without pinching or growth regulators.

*Total number of branches having a length of 5 mm or greater.*—Approximately 55.

*Branch length.*—Approximately 19.3 cm.

*Branch diameter.*—Approximately 8 mm.

*Internode length.*—Approximately 4.5 cm.

*Stem color.*—Yellow-Green Group 144D overlaid with Greyed-Purple Group 183B at nodes.

*Height of plant.*—The height of the foliage only, measuring approximately 17 cm above a 20 cm pot.

*Length of plant.*—The foliage of the plant from the rim of the pot to the tip of the longest trailing branch is approximately 17 cm.

*Area of spread.*—Approximately 45 cm with three plants per 20 cm pot.

Foliage description:

*Form.*—Ovate with acuminate apex and cuneate base.

*Margin.*—Serrate, ciliate.

*Arrangement.*—Opposite.

*Venation pattern.*—Pinnate.

*Surface.*—Smooth.

*Color of mature foliage—upper surface.*—Between Green Group 137A and Green Group 146A with veins of Yellow-Green Group 145C.

*Color of mature foliage—lower surface.*—Closest to Green Group 138B with veins of Yellow-Green Group 144C.

*Size.*—Approximately 6.3 cm in length; approximately 2.4 cm in width.

*Petiole length.*—1.1 cm.

*Petiole diameter.*—2 mm.

*Petiole texture.*—Smooth.

*Petiole color.*—Yellow-Green Group 145C with faint overlay of Red Group 52B at base.

Flower description:

*Flowering habit.*—Balfafusia is freely flowering under outdoor growing conditions with substantially continuous blooming from spring until fall. Inflorescences last above five (5) days.

*Flowers borne.*—Above foliage arising from leaf axils.

*Peduncle length.*—4.9 cm.

*Peduncle texture.*—Smooth.

*Peduncle color.*—Yellow-Green Group 145C with slight overlay of Red Group 52B on lower third.

*Flower form.*—Single.

*Quantity of flowers.*—Approximately 26 per plant.

*Flower size.*—Approximately 4.6 cm in diameter.

*Number of petals.*—Five.

*Petal texture.*—Smooth.

*Petal shape.*—Obovate.

*Petal margin.*—Entire.

*Petal apex.*—Superior petal is flat; other four petals are emarginate.

*Petal base.*—Superior petal has very broad base; other petals have narrow, pointed base.

*Petal length.*—Superior petal is 1.8 cm; other four petals are 2.6 cm.

*Petal width.*—Superior petal is 2.4 cm; other four petals are 2.1 cm.

*Flower color.*—Upper surface of all petals is closest to but bluer than 74A. The two lateral petals have bases and midribs of 74A, the two lower petals have bases of 74A, midribs and small area of 71A just above the bases. The lower surface of all petals is closest to 71C.

*Flower bud shape.*—Ovate.

*Flower bud length.*—1.7 cm.

*Flower bud diameter.*—8.3 mm.

*Flower bud color.*—Closest to Red-Purple Group 71B.

*Sepals*.—Three plus two rudimentary sepals fused into the under surface of the superior petal. Sepal texture is smooth, except along midrib which is sparsely pubescent. Inferior sepal color is 145D with slightly overlay of 72C at the margin, inferior sepal is 72C. A spur originating from the base of the inferior sepal is approximately 5.5 cm in length of fully opened flowers. The spur color is Red-Purple Group 58A with Yellow-Green Group 144C at tip.

*Reproductive organs*.—The stamens and anthers are fused together forming one organ that surrounds the pistil. There are five (5) stamens approximately 0.6 cm in length and 71B in color. The pistil is approximately 5 mm long, the stigma color is Yellow-Green Group 144D, the ovary color is Yellow-Green Group 144A. Generally, the anthers shed pollen prior to the stigma becoming receptive. The pollen color is Yellow Group 13D.

*Seed production*.—Seed production has not been observed.

*Disease and pest resistance*.—Disease and pest resistance have not been observed.

*Hardiness zone*.—'Balfafusia' is hardy in zones nine (9) and above.

What is claimed is:

1. A new and distinct cultivar of New Guinea Impatiens plant named 'Balfafusia' substantially as herein shown and described, which:

(a) Exhibits a unique trailing growth habit, (b) Forms medium green foliage, and (c) Exhibits a good basal branching character.

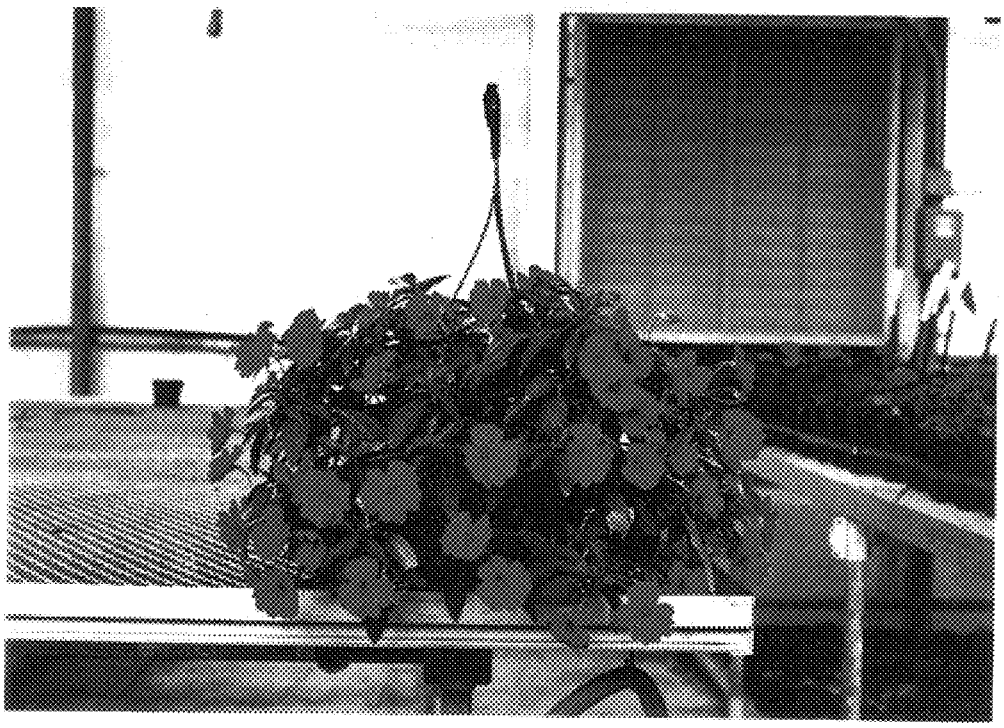

* * * * *